United States Patent
Cannell

(10) Patent No.: US 9,402,742 B2
(45) Date of Patent: Aug. 2, 2016

(54) MEDICAL DEVICE AND METHOD

(75) Inventor: Matthew Cannell, Warwickshire (GB)

(73) Assignee: T.J. Smith & Nephew Limited, Hull (GB)

( * ) Notice: Subject to any disclaimer, the term of this patent is extended or adjusted under 35 U.S.C. 154(b) by 492 days.

(21) Appl. No.: 13/997,120

(22) PCT Filed: Dec. 22, 2011

(86) PCT No.: PCT/GB2011/052554
§ 371 (c)(1),
(2), (4) Date: Jan. 22, 2014

(87) PCT Pub. No.: WO2012/085578
PCT Pub. Date: Jun. 28, 2012

(65) Prior Publication Data
US 2014/0135777 A1    May 15, 2014

(30) Foreign Application Priority Data
Dec. 24, 2010   (GB) .................................. 1021953.3

(51) Int. Cl.
*A61F 2/46* (2006.01)
*A61B 17/88* (2006.01)
*A61B 17/92* (2006.01)
(Continued)

(52) U.S. Cl.
CPC . *A61F 2/46* (2013.01); *A61B 17/88* (2013.01); *A61B 17/8866* (2013.01); *A61B 17/8872* (2013.01); *A61B 17/92* (2013.01); *A61F 2/4609* (2013.01); *A61F 2/4637* (2013.01); *A61B 2017/922* (2013.01); *A61F 2/34* (2013.01); *A61F 2/3609* (2013.01); *A61F 2/4607* (2013.01); *A61F 2002/30589* (2013.01); *A61F 2002/3446* (2013.01); *A61F 2002/4627* (2013.01); *A61F 2002/4685* (2013.01)

(58) Field of Classification Search
CPC ............... A61B 2017/0237; A61B 2017/0243; A61B 17/88; A61B 17/8872; A61B 17/92; A61B 2017/922; A61F 2/4607; A61F 2/4609; A61F 2002/4627; A61F 2/4637; A61F 2002/4685
See application file for complete search history.

(56) References Cited

U.S. PATENT DOCUMENTS

| | | | | |
|---|---|---|---|---|
| 6,447,443 B1 * | 9/2002 | Keogh | ............... | A61B 17/0206 128/898 |
| 2005/0137603 A1 * | 6/2005 | Belew | .................. | A61F 2/4609 606/91 |

(Continued)

FOREIGN PATENT DOCUMENTS

| | | | | |
|---|---|---|---|---|
| CH | WO 2010037685 A1 * | 4/2010 | ............ | A61F 2/4609 |
| FR | 2 877 210 A1 | 5/2006 | | |

(Continued)

OTHER PUBLICATIONS

Machine Translation of FR 2877210 A1 Retreived from <http://translationportal.epo.org/emtp/translate/?ACTION=description-retrieval&COUNTRY=FR&ENGINE=google&FORMAT=docdb&KIND=A1&LOCALE=en_EP&NUMBER=2877210&OPS=ops.epo.org/3.1&SRCLANG=fr&TRGLANG=en> on Nov. 16, 2015.*

(Continued)

*Primary Examiner* — Larry E Waggle, Jr.
(74) *Attorney, Agent, or Firm* — Taft Stettinius & Hollister LLP

(57) ABSTRACT

A device for attaching to an object including a portion attached to an object, and a vacuum generating means for generating a vacuum between the object and the portion to thereby attach the object to the device.

27 Claims, 8 Drawing Sheets

(51) Int. Cl.
  *A61F 2/34* (2006.01)
  *A61F 2/36* (2006.01)
  *A61F 2/30* (2006.01)

(56) References Cited

U.S. PATENT DOCUMENTS

2009/0216240 A1    8/2009  Posdal
2009/0281550 A1*  11/2009  Keller .................. A61F 2/4609
                                                        606/99
2011/0288649 A1*  11/2011  Ratzel .................. A61F 2/4637
                                                        623/22.24
2012/0059383 A1*   3/2012  Murphy ................ A61F 2/4612
                                                        606/99

FOREIGN PATENT DOCUMENTS

FR           2877210 A1 *  5/2006  ............ A61F 2/4609
WO    WO 2010/052500 A2    5/2010

OTHER PUBLICATIONS

Machine Translation of WO 2010037685 A1 Retreived from <https://patentscope.wipo.int/search/en/detail.jsf?docId=WO2010037685&recNum=1&maxRec=&office=&prevFilter=&sortOption=&queryString=&tab=PCTDescription> on Nov. 16, 2015.*

International Search Report; PCT/GB2011/052554; Feb. 21, 2012; 5 pages.

* cited by examiner

MEDICAL DEVICE AND METHOD

CROSS REFERENCE TO RELATED APPLICATIONS

The present application is a U.S. National Phase of International PCT Application No. PCT/GB2011/052554 filed on Dec. 22, 2011, which claims priority to Great Britain Patent Application No. GB 1021953.3 filed on Dec. 24, 2010, the contents of each application hereby incorporated by reference in its entirety.

FIELD OF THE INVENTION

The present invention relates to a medical device and method, in particular a medical device and method for manipulating and inserting an object such as an implant including, for example, an acetabular shell and/or liner.

BACKGROUND

During hip replacement surgery, it is often necessary to implant an acetabular component. Traditionally, these components include separate shells and liners. A shell is first implanted into the acetabulum with the use of an introducer which could connect to features on the inside of the shell. A liner (typically manufactured from plastic, ceramic or metal) may then be inserted into the shell. The liner provides the required bearing surface, and also covers the features on the inside of the shell used for connection to the introducer.

Modern hip replacement techniques have resulted in implants having a much reduced component wall thickness. As a result of this monoblock, metal components and pre-assembled shell and liner components are frequently used. With such components, it is necessary to ensure that the bearing surface is not compromised by the attachment method.

The introducer implant assembly needs to be secure enough to allow the implant to be fully inserted into the prepared acetabulum. The introducer also needs to be able to rotate and reposition the implant as required following insertion.

A known device and method involves the use of wires connected to the implant which can then be connected to an introducer.

Other known devices and methods involve the use of various designs of hard attachment.

Such known "wired" or "hard attachment" devices and methods have the disadvantage that they require additional features to be machined on the implant, causing additional complexity and expense.

It is also known to use a suction introducer, whereby the implant is attached to the introducer by means of suction. This type of device requires fixation to an external vacuum pipe to maintain constant suction. Obviously, this is disadvantageous in that such devices can only be used where there are compatible external vacuum sources. It is also disadvantageous having pipes/tubing in the surgical environment because they can be obstructive to the operating procedures. If the pipes/tubing become disconnected, tangled or otherwise constricted there can be a loss of suction resulting in disconnection of the implant from the introducer.

SUMMARY

According to a first aspect of the present invention, there is provided a device for attaching to an object, comprising:
  a portion for attachment to an object; and
  a vacuum generating means for generating a vacuum between the object and the portion to thereby attach the object to the device.

According to preferred embodiments of the present invention, the object is an implant.

An advantage of the present invention is that it removes the need for any additional features to be included on the implant.

According to a second aspect of the present invention, there is provided a device for attaching to an object, comprising:
  a portion for attachment to an object; and
  a vacuum generating means for generating a vacuum between the object and the portion to thereby attach the object to the device, wherein the vacuum generating means is integral to the device.

In the present application, an integral vacuum generating means is a means for generating a vacuum that does not involve an external negative pressure source i.e. vacuum source. Accordingly, no external pumps and connecting pipes are required.

An advantage of the present invention is that it removes the need for compatible external vacuum sources. This increases the flexibility, maneuverability and portability of the present device and significantly reduces costs. As it does not involve an external vacuum source, there are no associated vacuum pipes that can interfere in the surgical process and hence the present invention is readily maneuverable.

According to preferred embodiments of the present invention, the object is an implant.

An advantage of the present invention is that it removes the need for any additional features to be included on the implant.

The vacuum generating means may be mechanical.

According to a preferred embodiment of the present invention, the vacuum generating means comprises a moveable barrier disposed, in use, between the portion and the object, such that a volume is defined between the object, portion and barrier, and the barrier can be moved so as to increase or decrease the volume, thereby increasing or decreasing the vacuum.

If the volume between the object, the portion and the barrier is increased, the pressure necessarily decreases and hence the vacuum increases and the attachment strength increases. If the volume is decreased, the pressure necessarily increases and hence the vacuum decreases and the attachment strength decreases until there is no longer a sufficient vacuum to enable attachment.

The moveable barrier may be a flexible material.
The moveable barrier may be a flexible membrane.
The moveable barrier may be a ring.
The moveable barrier may be a band.
The moveable barrier may be a partial hemisphere. That is, the moveable barrier may be based on a hemisphere with the polar region removed to leave an equatorial ring or band.

An advantage of the moveable barrier being a ring, band, partial hemisphere, or the like, is that it minimizes the amount of material utilized, while still achieving the required vacuum. Accordingly, there is a savings on material costs, which means that the material can be readily replaced should replacement prove necessary. In addition, if the material is re-used, it can be readily cleaned due to the reduced surface area compared to a complete hemisphere, for example. Furthermore, minimizing the amount of moveable barrier material minimizes the risk of potential failure of the barrier because there is less surface area that can be potentially damaged/breached which would otherwise result in a loss of vacuum.

The moveable barrier may be a silicone material.

The moveable barrier may be a silicone seal.

The moveable barrier may be a thermoplastic elastomer.

According to an embodiment of the present invention, there is provided an actuator that moves the barrier.

The actuator may comprise a shaft attached to the barrier that can move with respect to the portion, thereby moving the barrier with respect to the portion.

The actuator may be moved manually.

The actuator may be moved automatically.

The vacuum generating means may be electromechanical.

The vacuum generating means may comprise an electromechanical pump.

The vacuum generating means may be battery powered.

The portion may comprise a surface that corresponds to an object surface.

Preferably, the object specified in any of the above aspects or embodiments of the invention is an implant.

The implant may be a shell. The implant may be an acetabular shell.

The implant may be a monoblock.

The implant may be pre-assembled.

The implant may be a liner. The implant may be an acetabular liner.

The implant may be a pre-assembled shell and liner.

The implant may be a head component. The implant may be a femoral head component. The head component may be connected to a stem, for example a hip stem.

According to a third aspect of the present invention, there is provided a method of attachment to an object, comprising:
  providing a device according to the first or second aspects of the present invention;
  disposing an object with respect to the portion;
  using the vacuum generating means to generate a vacuum between the object and the portion, thereby attaching the object to the device.

According to preferred embodiments of the present invention, the object is an implant.

The embodiments of the invention described above in relation to the first and second aspects of the present invention also apply to the third aspect of the present invention.

BRIEF DESCRIPTION OF THE DRAWINGS

Reference will now be made, by way of example, to the accompanying figures, in which.

DESCRIPTION OF THE ILLUSTRATED EMBODIMENTS

Figure 1:
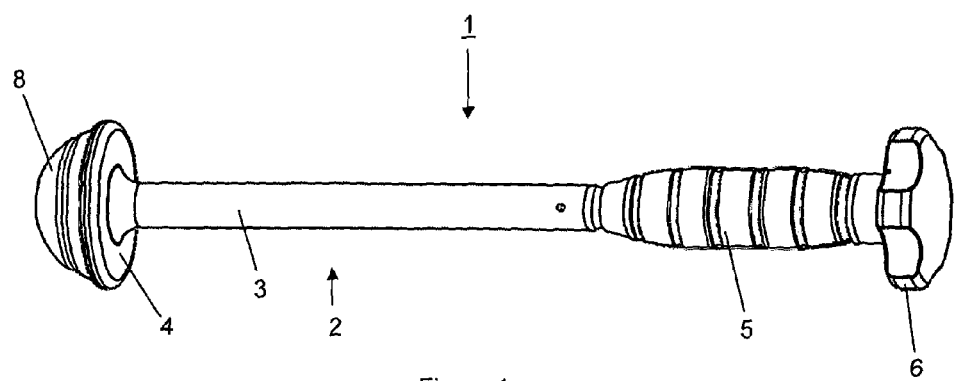
FIG. 1 shows a device according to an embodiment of the present invention.
Figure 2:
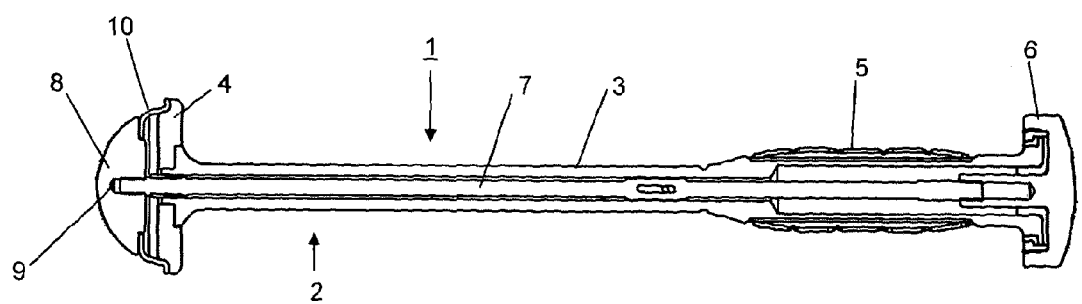
FIG. 2 shows a cross-section of the device of FIG. 1.
Figure 3:
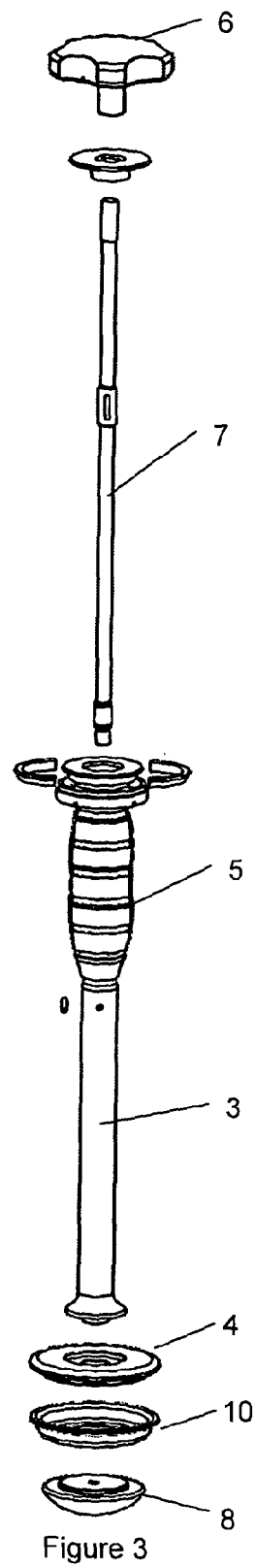
FIG. 3 shows an exploded view of the device of FIG. 1.
Figure 4:
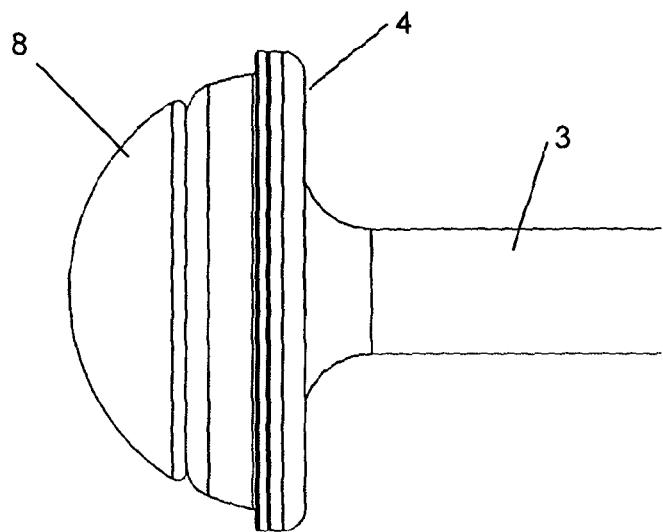
FIG. 4 shows the distal end of the device of FIG. 1.
Figure 5:
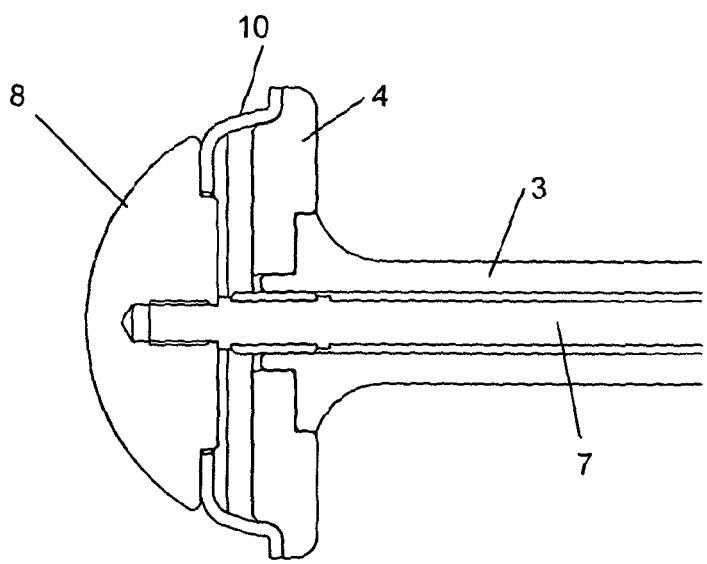
FIG. 5 shows a cross-section of the distal end of the device shown in FIG. 4.
Figure 6:
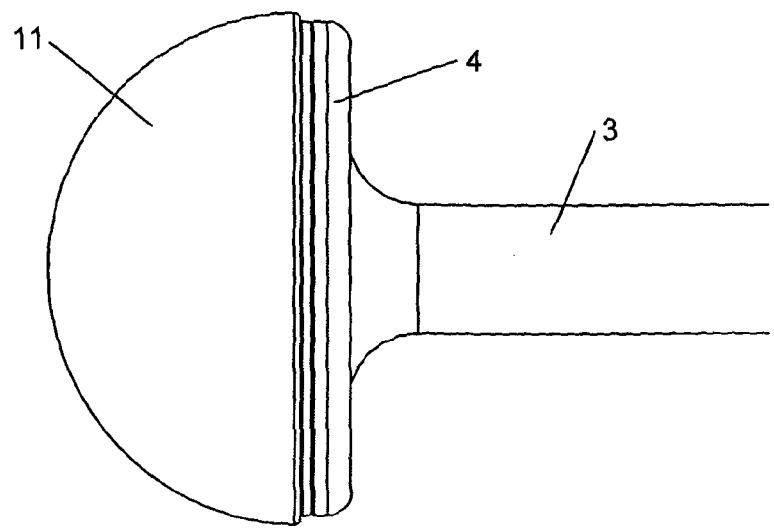
FIG. 6 shows the distal end of the device of FIG. 1 with an implant attached.
Figure 7:
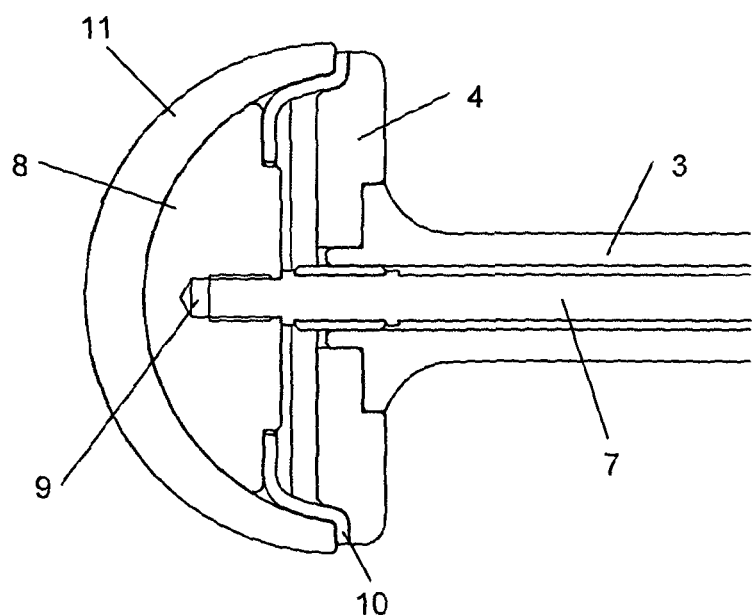
FIG. 7 shows a cross-section of the distal end of the device/implant combination shown in FIG. 6.

FIGS. 1-11 show a device (1) according to an embodiment of the present invention. The device comprises a portion (4,8,10) for attaching to an implant (11), and a vacuum generating means (6-10) for generating a vacuum between the implant (11) and the portion (4,8,10), thereby attaching the implant (11) to the device (1).

The device (1) of FIGS. 1-11 comprises a main body (2) having an open cylinder (3) with a base (4), which acts as an impaction plate, at the distal end of the cylinder, together with a handle (5) and knob (6) assembly at the proximal end of the cylinder (3) (see in particular FIGS. 1 to 3, 8 and 10). As shown in FIGS. 2, 3, 5, and 7 to 11, an actuator (7), in the form of a shaft or central rod (7), is disposed within the cylinder (3). The proximal end of the central rod (7) is threaded into the knob (6), such that when the knob (6) is rotated, it causes the central rod (7) to retract back along the axis of the main body (2) in a proximal direction (see FIGS. 8 and 10).

The device (1) of FIGS. 1-11 also comprises a cap (8) connected to the main body (2) via a locking screw (9) on the distal end of the central rod (7). The cap (8) is attached to a moveable barrier (10) in the form of a flexible ring or band (10), which is also attached to the base (4). The profile of the cap (8) and flexible ring or band (10) are designed such that they provide a tight fit to the inside profile of the implant (11).

Figure 8:
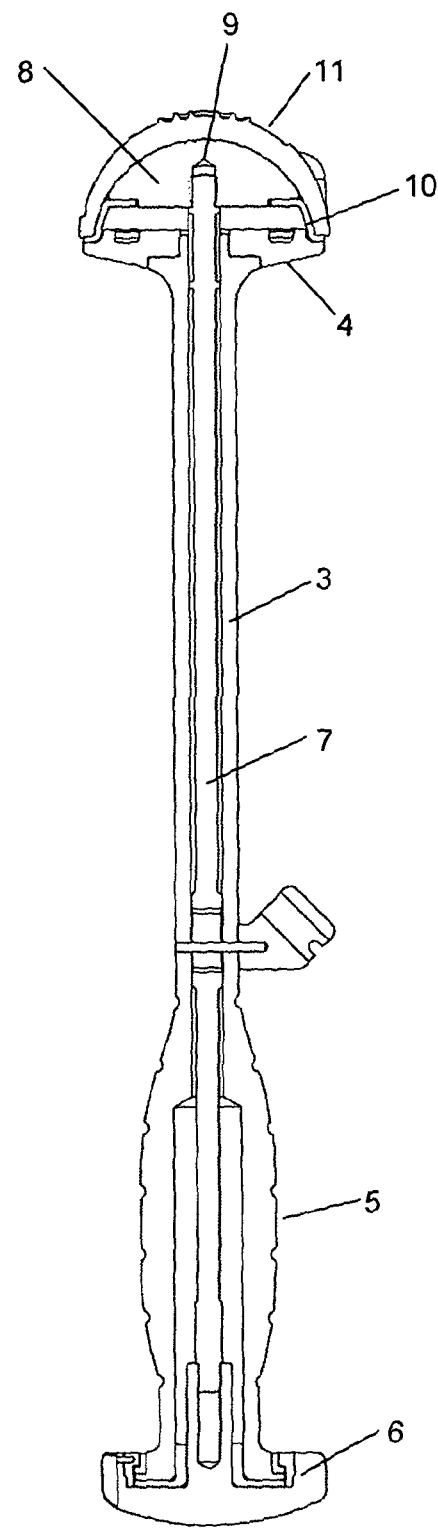
FIG. 8 shows a cross-section of the device/implant combination before vacuum generation.
Figure 9:
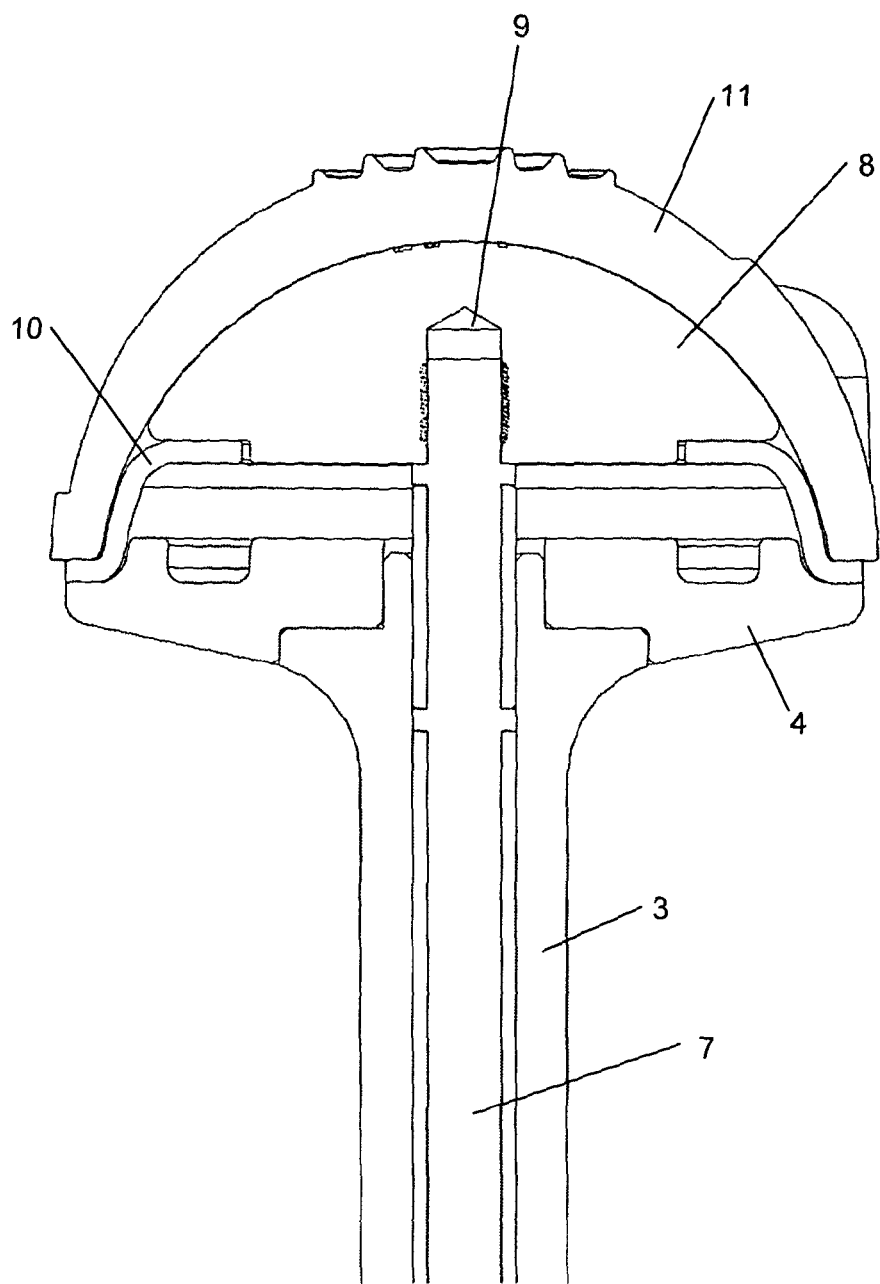
FIG. 9 shows an enlarged view of the distal end of the device/implant combination shown in FIG. 8.
Figure 10:
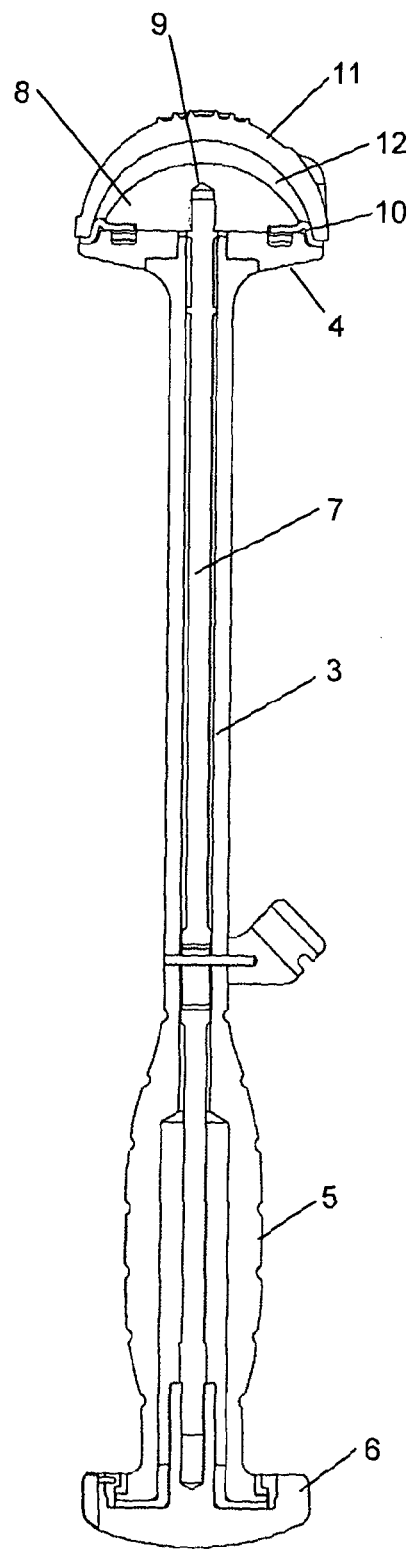
FIG. 10 shows a cross-section of the device/implant combination after vacuum generation.
Figure 11:
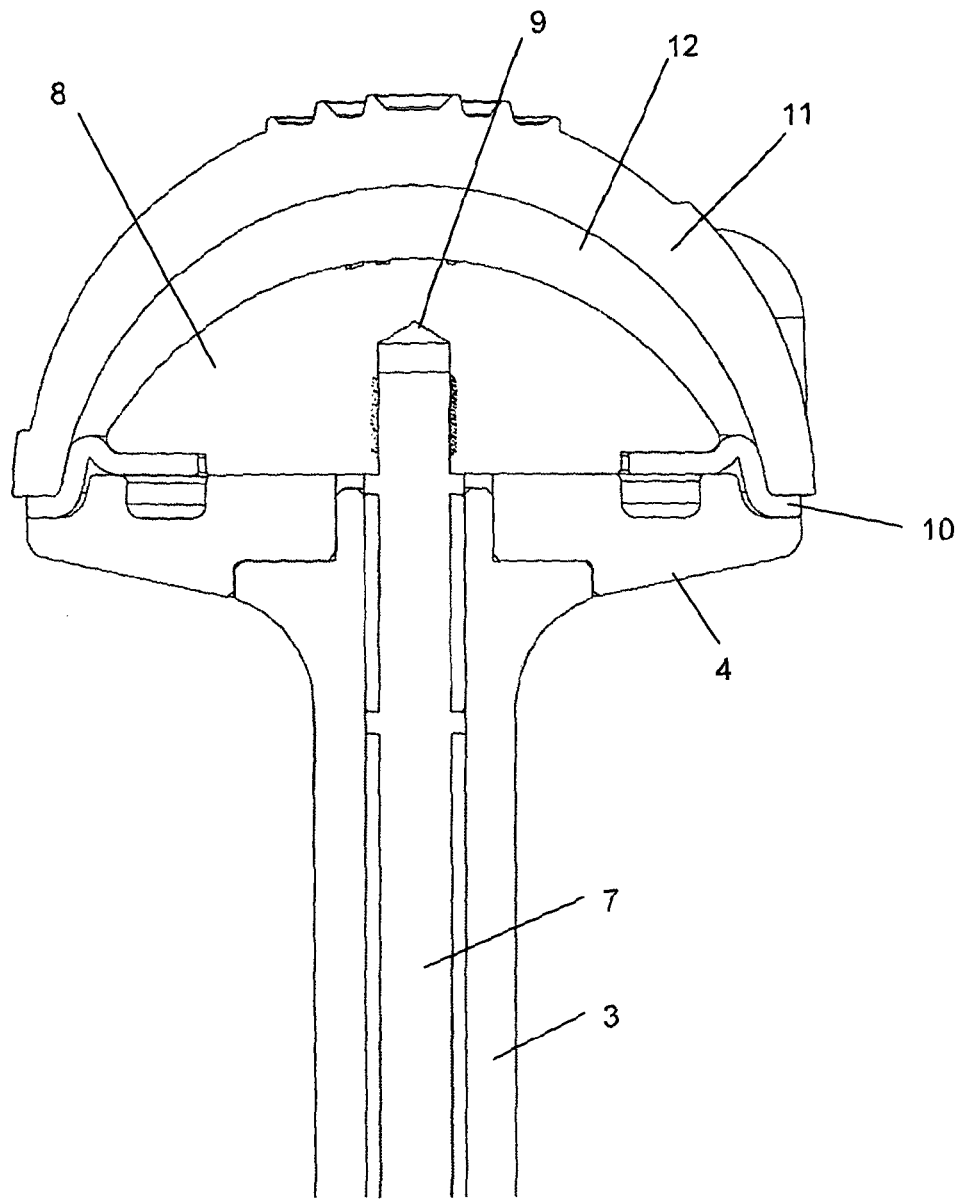
FIG. 11 shows an enlarged view of the distal end of the device/implant combination shown in FIG. 10.

When the device (1) is activated, the cap (8) and locking screw (9) assembly is drawn axially towards the base (4), causing the flexible ring or band (10) to deform within the construct (see FIG. 11). This action causes a vacuum to be created within the space (12) between the device (1) and the implant (11). It is this vacuum that causes the connection of the implant (11) to the device (1). FIGS. 8 and 9 show the device (1) before activation and FIGS. 10 and 11 show the device (1) after activation. As shown in FIGS. 10 and 11, a void (12) is formed between the device (1) and the implant (11).

The device (1) can then be used to impact the implant (11) into the prepared surgical site, for example an acetabulum. The body (2) and base (4) can transfer load/force applied to the handle (5)/knob (6) assembly to the implant (11).

The device (1) and implant (11) can be disconnected by reversing the rotation on the knob (6), which in turn decreases the vacuum until there is insufficient suction and separation is effected.

If required, the device (1) can then be reattached to the implant (11) in the body and used to reposition the implant (11).

Devices according to the present invention may also be used as a liner inserter for an implant design which requires the shell to be first inserted into the acetabulum and then a separate liner inserted.

A modification of the device could also enable a similar instrument to be used for head impaction.

A modification of the device could also enable stem insertion for Total Hip Arthroplasty.

Devices according to the present invention allow the implant to be attached to an introducer without the need for any attachment features on the implant. The device attaches to the implant with the use of suction, which is generated by the device itself.

Devices according to the present invention may be attached using different sized adaptors to a range of implant sizes.

Device according to the present invention enable impaction of the implant without damaging the bearing surface.

For devices according to the present invention, no external attachment features are required on the implant itself, which provides advantages over existing wired or hard attachment cup introducers. The implant itself is simpler to manufacture. Attachment features can provide a possible weakness to the implant and can also potentially cause soft tissue irritation.

Compared to known suction impactors, devices according to the present invention have the advantage that no external suction source is required. This prevents the need for additional tubes to be connected, making the instrument easier to use in a surgical environment. It also eliminates the possibility of the tubes becoming loose, tangled or constricted (resulting in a loss of vacuum) or otherwise obstructive to the surgical activity.

As mentioned above, an advantage of those embodiments in which the moveable barrier is a ring, band, partial hemisphere, or the like, is that it minimizes the amount of material utilized, while still achieving the required vacuum. Accordingly, there is a savings on material costs, which means that the material can be readily replaced should replacement prove necessary. In addition, if the material is re-used, it can be readily cleaned due to the reduced surface area compared to a complete hemisphere, for example. Furthermore, minimizing the amount of moveable barrier material minimizes the risk of potential failure of the barrier because there is less surface area that can be potentially damaged/breached which would otherwise result in a loss of vacuum.

The invention claimed is:

1. A device for attaching to an object, comprising:
   a cap axially displaceable between a first position and a second position, the cap being shaped to abut against at least a portion of an inner surface of the object when at the first position, the cap being disengaged and separated from the inner surface by a space when the cap is at the second position; and
   a moveable barrier disposed between the cap and a base of the device, the moveable barrier structured to provide a seal about an adjacent portion of the inner surface of the object at least when the cap is at the second position, the seal structured to retain a vacuum in the space, the vacuum being increased as the cap is axially displaced from the first position to the second position, the object being securely attached to the device by a vacuum force of the vacuum at least when the cap is at the second position.

2. The device according to claim 1, wherein the device does not include an external vacuum source remote from the device, and wherein the cap exerts a compressive force against the moveable barrier at least when the cap is in the second position that deforms the moveable barrier in a manner that provides the seal.

3. The device according to claim 1, wherein the cap is coupled to an actuator, the actuator threadingly coupled to a knob, and further wherein rotational displacement of the knob adjusts a relative axial position of the actuator, thereby axially displacing the cap.

4. The device according to claim 1, wherein the space has an adjustable volume defined between at least the object and the cap, the adjustable volume being increased by axial displacement of the cap from the first position to the second position, and wherein the vacuum force is larger when the cap is at the second position than when the cap is at the first position.

5. The device according to claim 4, wherein the moveable barrier comprises a flexible membrane.

6. The device according to claim 4, wherein the moveable barrier is a partial hemisphere.

7. The device according to claim 4, wherein the moveable barrier is a band.

8. The device according to claim 4, wherein the moveable barrier is a ring.

9. The device according to claim 4, wherein the moveable barrier is a silicone seal.

10. The device according to claim 4, wherein the cap is coupled to an actuator, and further wherein axial displacement of the actuator is translated into axial displacement of the cap, which facilitates movement of the moveable barrier.

11. The device according to claim 10, wherein the actuator comprises a shaft coupled to the cap, the shaft being moveable with respect to the cap, thereby moving the moveable barrier relative to the cap.

12. The device according to claim 1, wherein the cap has a hemispherical shape that mates with a hemispherical shape of the inner surface of the object.

13. The device according to claim 1, wherein the moveable barrier comprises an annular ring positioned at least between about a periphery of a portion of the cap and against a portion of an elongated shaft.

14. The device according to claim 1, wherein the cap comprises a surface having a shape that corresponds to a shape of the inner surface of the object.

15. The device according to claim 1, wherein the object is an implant selected from a group consisting of an acetabular shell, an acetabular liner and a head component.

16. A medical device for attachment to an implant, comprising:
   an elongate shaft portion having a distal end and a proximal end;
   a vacuum generator having a cap and a moveable barrier, a portion of the moveable barrier positioned between the cap and the distal end of the elongated shaft portion, the vacuum generator structured to generate a vacuum in a space between the cap and the implant to attach the medical device to the implant via a suction force, at least a portion of the moveable barrier extending outside of the implant and being deformed by a compressive force generated by axial displacement of the cap to form a seal that retains the suction force in the space as the cap is axially displaced toward the distal end of the elongated shaft portion, and wherein a volume of the space increases as the cap is displaced toward the distal end of the elongated shaft portion, and further wherein the suction force of the vacuum increases as the volume of the space increases.

17. The medical device according to claim 16, wherein the vacuum generator does not include an external vacuum source remote from the device.

18. The medical device according to claim 16,
   wherein the cap is transitioned from a first position to a second position to thereby increase the volume of the space between the cap and a corresponding surface of the implant to create the vacuum to attach the device to the implant via the suction force.

19. The medical device according to claim 18, wherein the cap is displaced away from the corresponding surface of the implant to increase the volume of the space and to correspondingly increase the vacuum; and
   wherein the cap is displaced toward the corresponding surface of the implant to decrease the volume of the space and to correspondingly decrease the suction force of the vacuum.

20. The medical device according to claim 18, wherein the moveable barrier comprises a flexible membrane.

21. The medical device according to claim 20, wherein the cap is hemispherical shaped; and wherein the flexible membrane comprises an annular ring extending peripherally about the distal end.

22. The medical device according to claim 18, wherein the cap comprises a hemispherical shaped cap positioned adjacent a hemispherical shaped surface of the implant; and wherein the moveable barrier comprises an annular ring peripherally about a portion of the hemispherical shaped cap.

23. The medical device according to claim 18, further comprising an actuator structured to transition the cap between the first and second positions, the actuator comprising:

an actuator rod threadingly coupled to an actuator knob, the actuator rod extending through an interior of the elongate shaft portion, wherein rotation of the actuator knob is translated to axial displacement of the actuator rod; and wherein axial displacement of the actuator rod transitions the cap between the first and second positions.

24. The medical device according to claim 23, wherein the moveable barrier is attached to the actuator rod.

25. The medical device according to claim 16, wherein the cap is a hemispherical shaped cap positioned adjacent a corresponding hemispherical shaped surface of the implant and the moveable barrier is a flexible seal extending peripherally about a portion of the hemispherical shaped cap wherein the flexible seal is sealingly engaged against an annular portion of the implant.

26. The medical device according to claim 25, wherein the flexible seal comprises an annular ring.

27. The medical device according to claim 16, wherein the implant is selected from a group consisting of an acetabular shell, an acetabular liner, and a femoral head component.

* * * * *